(12) United States Patent
Ueno et al.

(10) Patent No.: US 10,405,394 B2
(45) Date of Patent: Sep. 3, 2019

(54) ILLUMINATION SYSTEM

(71) Applicant: Panasonic Intellectual Property Management Co., Ltd., Osaka (JP)

(72) Inventors: Saori Ueno, Osaka (JP); Kazuhiro Hatta, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 15/987,167

(22) Filed: May 23, 2018

(65) Prior Publication Data
US 2018/0352630 A1  Dec. 6, 2018

(30) Foreign Application Priority Data

May 30, 2017  (JP) ................................. 2017-106669

(51) Int. Cl.
- *A61N 5/06* (2006.01)
- *H05B 37/02* (2006.01)
- *H05B 33/08* (2006.01)

(52) U.S. Cl.
CPC ....... *H05B 33/0863* (2013.01); *A61N 5/0618* (2013.01); *H05B 33/0842* (2013.01); *H05B 33/0851* (2013.01); *H05B 37/0209* (2013.01); *H05B 37/0227* (2013.01); *H05B 37/0272* (2013.01); *H05B 37/0281* (2013.01); *A61N 2005/0626* (2013.01); *A61N 2005/0627* (2013.01); *A61N 2005/0652* (2013.01); *A61N 2005/0663* (2013.01)

(58) Field of Classification Search
None
See application file for complete search history.

(56) References Cited

U.S. PATENT DOCUMENTS

| 8,795,344 | B2* | 8/2014 | Baaijens | ............... A61M 21/00 607/88 |
| 9,137,867 | B2* | 9/2015 | Kamii | .................. H05B 33/086 |
| 9,579,521 | B2* | 2/2017 | Ferraz Rigo | ......... A61N 5/0618 |
| 10,252,022 | B2* | 4/2019 | Baaijens | ............. A61M 21/00 |
| 2010/0277105 | A1* | 11/2010 | Oyama | ................ A61N 5/0618 315/312 |
| 2012/0032616 | A1* | 2/2012 | Toda | ..................... A61M 21/00 315/360 |
| 2012/0097749 | A1* | 4/2012 | Lashina | ............... A61N 5/0618 236/51 |

(Continued)

FOREIGN PATENT DOCUMENTS

| JP | 2005259437 A | * | 9/2005 |
| JP | 2010-022672 A | | 2/2010 |

*Primary Examiner* — Vibol Tan
(74) *Attorney, Agent, or Firm* — McDermott Will & Emery LLP

(57) ABSTRACT

An illumination system includes a light source capable of emitting biorhythm control light, a controller that controls a lighting state of the light source, and a manipulation apparatus. The controller executes an introduction mode in which the illuminance of the biorhythm control light is set by gradually increasing or decreasing illuminance of the light source over time, and a stationary mode in which the illuminance of the light source is constantly maintained at the illuminance of the biorhythm control light.

12 Claims, 10 Drawing Sheets

(56) References Cited

U.S. PATENT DOCUMENTS

| | | | | |
|---|---|---|---|---|
| 2014/0052220 A1* | 2/2014 | Pedersen | ............... | A61N 5/0618 |
| | | | | 607/88 |
| 2014/0306620 A1* | 10/2014 | Maxik | ................ | H05B 33/0845 |
| | | | | 315/294 |
| 2015/0035440 A1* | 2/2015 | Spero | ....................... | B60Q 1/04 |
| | | | | 315/153 |
| 2015/0305126 A1* | 10/2015 | Maeda | ................ | H05B 37/0281 |
| | | | | 315/134 |
| 2016/0195856 A1* | 7/2016 | Spero | ..................... | G06N 5/046 |
| | | | | 700/90 |
| 2017/0031324 A1* | 2/2017 | Toda | ....................... | G04G 11/00 |
| 2017/0259080 A1* | 9/2017 | Fujiwara | ............... | A61N 5/0618 |

\* cited by examiner

ILLUMINATION SYSTEM

INCORPORATION BY REFERENCE

The entire disclosure of Japanese Patent Application No. 2017-106669 filed on May 30, 2017, including the specification, claims, drawings, and abstract, is incorporated herein by reference in its entirety.

BACKGROUND

Technical Field

The disclosure relates to an illumination system.

Background Art

In the related art, there is known phototherapy in which a biological clock is adjusted to regulate a biorhythm by exposing a patient under high-illuminance light close to sunlight, and several illumination systems for phototherapy have been proposed. For example, Japanese Unexamined Patent Application Publication No. 2010-22672 discloses a biorhythm-assisting illumination apparatus having a first light emitter that emits light of a wavelength band capable of providing a high melatonin-production-suppression effect, and a second light emitter that emits light of a wavelength band capable of providing a low melatonin-production-suppression effect.

In the phototherapy, exposure to an amount of light approximately 8 to 10 times that of normal illumination light is recommended. However, a user may feel uncomfortable for such a high illuminance environment due to unfamiliarity. In particular, when light having a color temperature higher than that of general illumination light is employed, such discomfort becomes more noticeable. For example, in order to realize high-quality sleep, it is preferable to reduce the illuminance of light to obtain a low color temperature before going to bed. However, similarly, a user may feel uncomfortable due to unfamiliarity in some cases. An object of the disclosure is to provide an illumination system capable of making a user smoothly familiar with a biorhythm illumination light environment.

SUMMARY

According to an aspect of the disclosure, there is provided an illumination system including: a light source configured to control general illumination light and biorhythm control light having an illuminance either higher or lower than that of the general illumination light; a controller is configured to control a lighting state of the light source; and a manipulation apparatus. The controller is further configured to execute an introduction mode in which the illuminance of the biorhythm control light is set by either increasing or decreasing the illuminance of the light source, and wherein the controller is further configured to execute a stationary mode in which the illuminance of the light source is maintained at the illuminance of the biorhythm control light.

Using the illumination system according to an aspect of the disclosure, it is possible to make a user smoothly familiar with the biorhythm illumination light.

BRIEF DESCRIPTION OF THE DRAWINGS

The figures depict one or more implementations in accordance with the present teachings, by way of example only, not by way of limitations. In the figures, like reference numerals refer to the same or similar elements.

DETAILED DESCRIPTION

An illumination system according to an embodiment of the disclosure will now be described in details with reference to the accompanying drawings. An illumination system described herein is not limited to those described in the following embodiments. In addition, it is assumed that each element may be selectively combined across a plurality of embodiments described below.

A main body of an apparatus and system described herein has a computer. A main function of the apparatus and system described herein is implemented by causing this computer to execute a program. The computer has a processor that operates depending on the program as a main hardware configuration. Any processor may be employed as long as it can implement the aforementioned function by executing a program. The processor includes at least one electronic circuit including an integrated circuit (IC) or a large-scale integrated circuit (LSI). A plurality of electronic circuits may be integrated into a single chip or a plurality of chips. A plurality of chips may be packaged in a single device or a plurality of devices. In addition, the program is stored in a non-transitory storage medium such as a computer-readable read-only memory (ROM), an optical disc, or a hard disk drive. The program may be stored in the storage medium in advance or may be supplied to the storage medium via a wide-area communication network such as the Internet.

Figure 1:
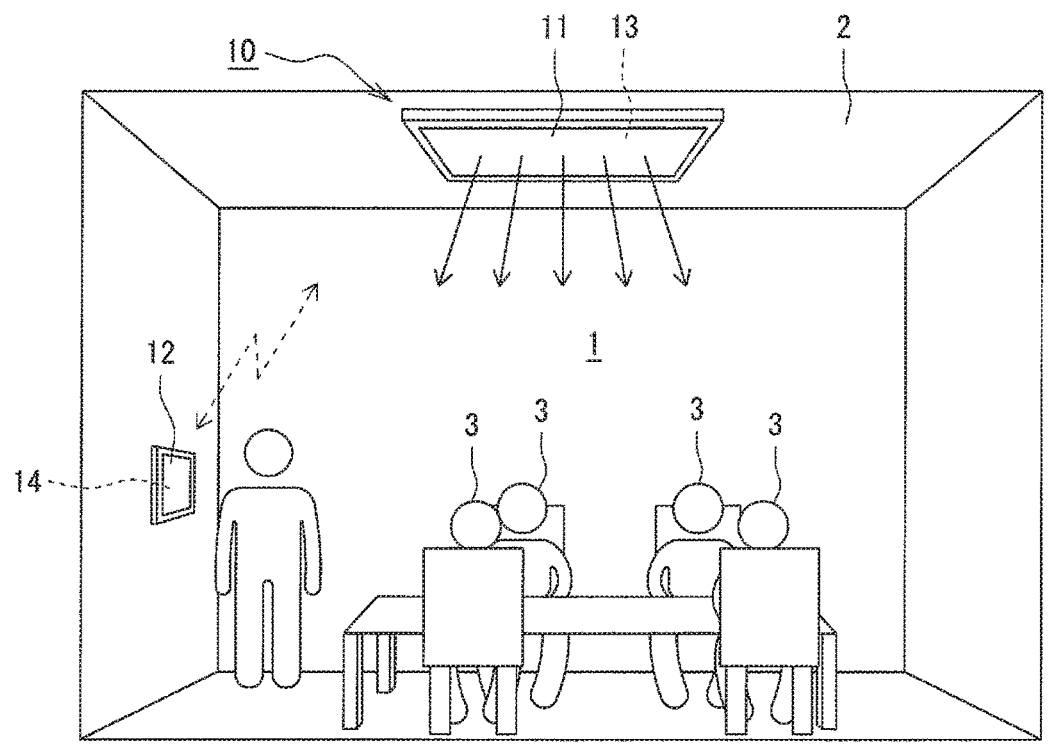
FIG. 1 is a diagram illustrating an illumination system according to an embodiment of the disclosure and an environment for using the illumination system.
Figure 2:
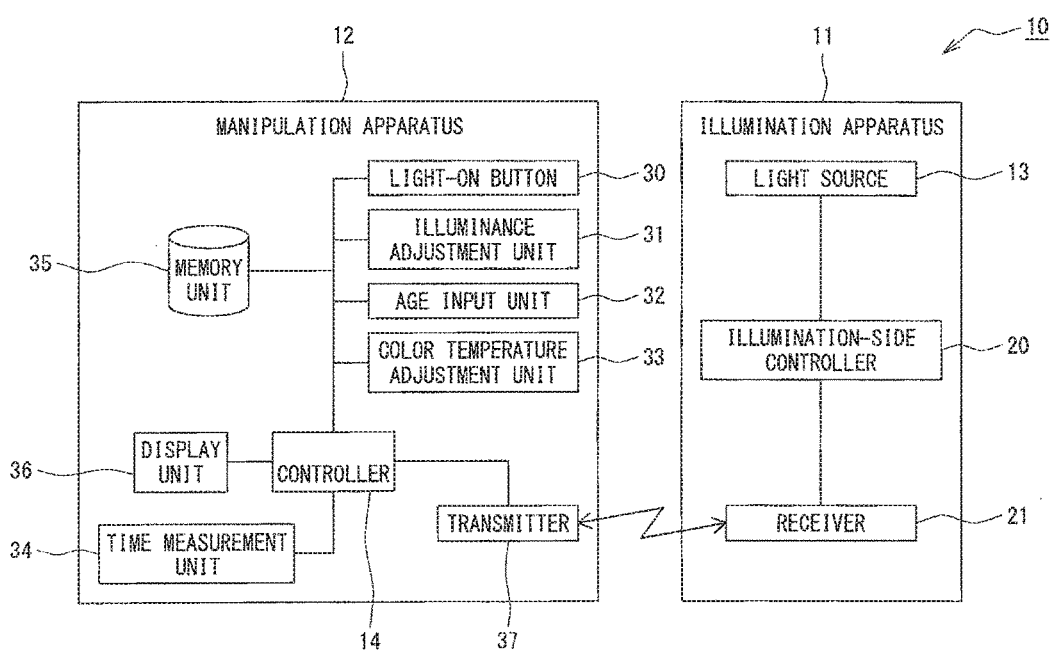
FIG. 2 is a block diagram illustrating a configuration of the illumination system according to an embodiment of the disclosure.

FIG. 1 is a diagram illustrating an illumination system 10 according to an embodiment of the disclosure and an environment for using the illumination system 10. FIG. 2 is a block diagram illustrating a configuration of the illumination system 10. As illustrated in FIGS. 1 and 2, the illumination system 10 includes an illumination apparatus 11 having a light source 13, and a manipulation apparatus 12 for manipulating the illumination apparatus 11. In addition, the illumination system 10 includes a controller 14 configured to control a lighting state of the light source 13. That is, the illumination system 10 includes the light source 13, the control unit 14, and the manipulation apparatus 12.

In the example of FIG. 1, the illumination apparatus 11 of the illumination system 10 is installed on a ceiling 2 of a room 1 where phototherapy target persons 3 are present. However, an installation place of the illumination apparatus 11 is not limited to the ceiling of the room. The illumination system 10 is suitable for a clinic, a hospital, an elderly welfare facility, or the like where phototherapy is executed. However, the illumination system 10 may also be installed in a general house, an office, a shop, or the like. The illumination system 10 may be installed outdoors, although it is usually installed indoors.

The light source 13 is a light source configured to emit general illumination light and biorhythm control light having illuminance higher or lower than the general illumination light. The biorhythm control light is light having an effect of regulating a daily life rhythm by adjusting a biological clock. The biorhythm control light may include, for example, illumination light having illuminance higher than that of the general illumination light (herein, referred to as "bioactive light") and illumination light having illuminance lower than that of the general illumination light (herein, referred to as "tranquility light").

The illuminance of the general illumination light irradiated from the light source 13 is set to, for example, 100 (1x) to 700 (1x), and preferably, 300 (1x) to 700 (1x) and may be changed within this range. In addition, in a case where a plurality of light sources 13 are provided, the illuminance of the light sources 13 refers to a total illuminance of all of the light sources 13 in a lighting state; that is, illuminance of the entire illumination apparatus 11 unless specified otherwise.

The light source 13 can emit bioactive light having illuminance higher than that of the general illumination light as the biorhythm control light. The illuminance of the bioactive light is set to, for example, three times or more, preferably five times or more, and particularly preferably eight to ten times the illuminance of the general illumination light. A preferable example of the illuminance of the bioactive light is approximately 1,000 (1x) or higher, and particularly preferably 2,500 (1x). The bioactive light has an effect of suppressing secretion of melatonin, which is a hormone responsible for drowsiness. The bioactive light affects the autonomic nervous system and activates the sympathetic nervous system, so as to reset the biological clock.

The light source 13 may emit tranquility light having an illuminance lower than that of the general illumination light as the biorhythm control light. The tranquility light has illuminance of, for example, 0.5 times or less, and preferably, 0.05 to 0.3 times the illuminance of the general illumination light. Preferably, the tranquility light has an illuminance lower than 50 (1x), and particularly preferably, 1 (1x) to 30 (1x). The tranquility light has an effect of leading a user to high-quality sleep by suitably stimulating melatonin secretion without disturbance.

The illumination system 10 is preferably employed as a phototherapy illumination system as described above. Although described below in more detail, the illumination system 10 helps a user to be smoothly familiar to the biorhythm illumination light environment without feeling uncomfortable. When a human being is exposed to bright light, the biological clock is reset, and melatonin secretion is suppressed, so that melatonin is secreted after a certain period of time. In the phototherapy, the melatonin secretion timing is controlled using light, so that a daily life rhythm is regulated by adjusting the biological clock. The phototherapy is said to be effective for a sleep disorder, insomnia of the elderly, dementia, depression, and the like. Phototherapy using high illuminance light (bioactive light) is also called "high-illuminance phototherapy."

The light source 13 emits white light. However, the bioactive light preferably contains at least a blue light component having a wavelength of 430 to 490 nm. Since the blue light is known to suppress melatonin secretion to a high degree, melatonin secretion can be suppressed efficiently by using bioactive light containing blue light. Meanwhile, the tranquility light preferably contains no blue light or has a low color temperature having little blue light component. The illumination system 10 may have a plurality of light sources 13 from which different wavelengths of light are emitted, and the light source 13 to be turned on may be changed depending on the type of light to be emitted.

The type of the light source 13 is not particularly limited as long as it can emit general illumination light and biorhythm control light such as bioactive light. Preferably, a semiconductor light-emitting element is employed. A preferable example of the semiconductor light-emitting element is a light-emitting diode (LED). The light-emitting element may be sealed with a sealing layer including a fluorescent substance. The light source 13 converts part of the blue light of the light-emitting element into light having a longer wavelength, for example, using a fluorescent substance, and emits white light by mixing the remaining part of the blue light with the white light.

The light source 13 may include at least a first light source that emits blue light and a second light source that emits light having a ratio of the blue light smaller than that of the first light source. Alternatively, the light source 13 may include a high color temperature light source and a low color temperature light source that emits light having a color temperature lower than that of the high color temperature light source. By using a plurality of light sources capable of emitting different wavelengths of light (color temperatures), it is possible to facilitate reduction of a user's discomfort while maintaining the effect of the biorhythm control light.

The controller 14 is further configured to execute an introduction mode in which the illuminance of the biorhythm control light is obtained by increasing or decreasing the illuminance of the light source 13, and a stationary mode in which the illuminance of the light source 13 is maintained at the illuminance of the biorhythm control light. By executing the introduction mode, it is possible to prevent an abrupt change of the illuminance of the light source 13 and make a user slowly familiar with the biorhythm control light illumination environment. In the introduction mode, the color temperature of the illumination light may gradually change along with the illuminance of the light source 13.

Note that the controller 14 may execute a general illumination mode in which general illumination light is emitted.

The controller 14 is further configured to execute an intensification mode in which the illuminance of the bioactive light is set by increasing the light of light source 13 as the introduction mode. Since the bioactive light has illuminance remarkably higher than that of the general illumination light, the bioactive light illumination environment easily makes a user feel uncomfortable. However, by executing the intensification mode, it is possible to reduce discomfort and make a user smoothly familiar with such an illumination environment. In addition, the controller 14 may directly switch to the general illumination light when the bioactive light environment is returned to the general illumination light environment. However, it is preferable to execute a reduction mode in which the illuminance of the light source 13 is reduced from the illuminance of the bioactive light to the illuminance of the general illumination light.

The controller 14 may execute a tranquility light introduction mode in which the illuminance of the tranquility light is obtained by gradually decreasing the illuminance of the light source 13 over time as the introduction mode. Since the tranquility light has illuminance remarkably lower than that of the general illumination light, a user may feel uncomfortable when the general illumination light environment is abruptly switched to the tranquility light illumination environment. However, by executing the tranquility light introduction mode, it is possible to reduce discomfort and make a user smoothly familiar with such an illumination environment.

As described above, the illumination system 10 has the illumination apparatus 11 and the manipulation apparatus 12. Although one illumination apparatus 11 and one manipulation apparatus 12 are provided in the room 1 in the example of FIG. 1, a plurality of illumination apparatuses 11 and a plurality of manipulation apparatuses 12 may exist. A plurality of illumination apparatuses 11 may be provided in the same room, and a plurality of illumination apparatuses 11 may be operated using a single manipulation apparatus 12. Alternatively, a plurality of manipulation apparatuses 12 may be used to control a single illumination apparatus 11.

The illumination apparatus 11 has a light source 13, an illumination-side controller 20, and a receiver 21. The light source 13 is not particularly limited as long as it can emit the general illumination light and the biorhythm control light. Preferably, a light-emitting diode (LED) is employed. The illumination-side controller 20 controls a lighting state of the light source 13 in response to a control command received from the manipulation apparatus 12. In a case where the light source 13 is an LED, the illumination-side controller 20 has a constant current circuit for constantly maintaining the electric current flowing to the light source 13, so that the current flowing to the light source 13 is controlled by the constant current circuit.

The receiver 21 receives a radio signal transmitted from the manipulation apparatus 12. According to an embodiment of the disclosure, this radio signal contains a control command created by the controller 14. Note that the illumination apparatus 11 may be connected to the manipulation apparatus 12 in a wired manner. Alternatively, the illumination system 10 has both the manipulation apparatus 12 connected to the illumination apparatus 11 in a wired manner and the manipulation apparatus 12 connected in a wireless manner.

The illumination system 10 has, for example, a pulse width modulation (PWM) type light control function. In the intensification mode, a PWM signal is transmitted as a control command from the controller 14, and the illumination-side controller 20 controls the lighting state of the light source 13 in response to the PWM signal. In the intensification mode, the illuminance of the light source 13 gradually increases over time. Therefore, a duty ratio of the PWM signal gradually increases over time. Meanwhile, in the reduction mode, the illuminance of the light source 13 gradually decreases over time. Therefore, the duty ratio of the PWM signal gradually decreases over time.

According to an embodiment of the disclosure, the controller 14 having the function of executing the intensification mode or the like is provided in the manipulation apparatus 12, and the control command created by the manipulation apparatus 12 is transmitted to the illumination apparatus 11. Alternatively, the function of the controller 14 may be provided in the illumination-side controller 20. In addition, some elements of the illumination system 10 may be provided by one or more servers connected via a network such as the Internet. For example, all or some of the functions of the controller 14 may be provided by one or more servers.

The manipulation apparatus 12 is an apparatus for manipulating the illumination apparatus 11. For example, it is possible to turn on or off, dim, or tone the light source 13 by manipulating the manipulation apparatus 12. The manipulation apparatus 12 may be a wall light switch provided on a wall surface of the room 1 or may be a remote controller of the illumination system 10. Alternatively, the manipulation apparatus 12 may be adapted in a mobile device such as a smart phone or a tablet terminal. For example, in a phototherapy facility, a tablet terminal held by a staff member or the like may be used as the manipulation apparatus 12. In this case, a program (application software) for executing the function of the illumination system 10 may be installed in the tablet terminal or the like to provide the function of the manipulation apparatus 12.

The manipulation apparatus 12 has a light-on button 30 to turn on the light source 13. In addition, the light source 13 may be turned off by pressing the light-on button 30 when the light source 13 is turned on. The manipulation apparatus 12 has a display unit 36 such as a liquid crystal display or an organic electroluminescent display. In a case where a touch panel function is provided in the display unit 36, the light-on button 30 or the like is displayed on the display unit 36. That is, a manipulation screen for manipulating the lighting state of the light source 13 is displayed on the display unit 36. Note that the manipulation button such as the light-on button 30 may be a mechanical switch such as a pressing button.

The manipulation signal based on the manipulation on the light-on button 30 is transmitted to the controller 14, so that the lighting state of the light source 13 is controlled by virtue of the function of the controller 14 based on the manipulation signal. The controller 14 generates a control command based on the manipulation signal and transmits the control command to the illumination apparatus 11 via a transmitter 37. The illumination system 10 may start the introduction mode by turning on the light-on button 30. Alternatively, the general illumination mode or the introduction mode may be executed depending on how to manipulate the light-on button 30. For example, the general illumination light may be emitted by pressing the light-on button 30 once, or the introduction mode may start by pressing the light-on button 30 two times. In addition, a general illumination mode manipulation button and an introduction mode manipulation button may also be provided separately.

The manipulation apparatus 12 may have an illuminance adjustment unit 31 for reducing the illuminance of the light source 13, an age input unit 32 for inputting the age of a phototherapy target person 3 who is a target person to be irradiated with the bioactive light, and a color temperature adjustment unit 33 as manipulation units (manipulation buttons) for manipulating the light source 13. The color temperature adjustment unit 33 is a manipulation unit for reducing the color temperature of the light source 13. Alternatively, the illuminance of the light source 13 may increase by manipulating the illuminance adjustment unit 31, or the color temperature may increase by manipulating the color temperature adjustment unit 33. The manipulation apparatus 12 may have only one or two of the three manipulation units. A plurality of manipulation apparatuses 12 such as the wall light switch and the tablet terminal may be provided. For example, the light-on button 30 may be provided in the wall light switch, and the light-on button 30 and the three manipulation units may be provided in the tablet terminal.

The manipulation apparatus 12 has a time measurement unit 34 for measuring time used for the control of the controller 14, and a memory unit 35 for storing data or the like necessary for the control of the controller 14. The time measurement unit 34 may be configured as a part of the controller 14. The memory unit 35 preferably includes a non-transitory storage medium such as a computer-readable ROM, an optical disc, or a hard disk drive. The memory unit 35 stores a control parameter necessary in the control of the controller 14, such as input information of the age input unit 32, a control program for executing the control of the controller 14, and the like.

The controller 14 is configured to execute the introduction mode (including the intensification mode and the tranquility light introduction mode), the stationary mode, the tranquility light stationary mode, the reduction mode, and the general illumination mode. The controller 14 is built in a computer having one or more devices such as a processor (CPU), a memory, and an input/output port. In a case where the device of the manipulation apparatus 12 is shared with other systems, the computer serving as the controller 14 may also be shared with other systems. The function of the controller 14 may be implemented by executing a control program of the illumination system 10 stored in the memory unit 35.

Figure 3:
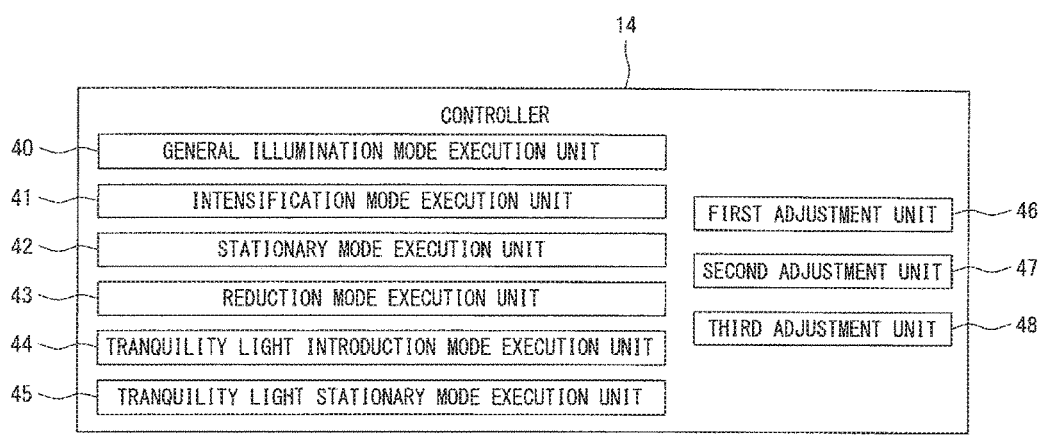
FIG. 3 is a block diagram illustrating a configuration of a controller according to an embodiment of the disclosure.
Figure 4:
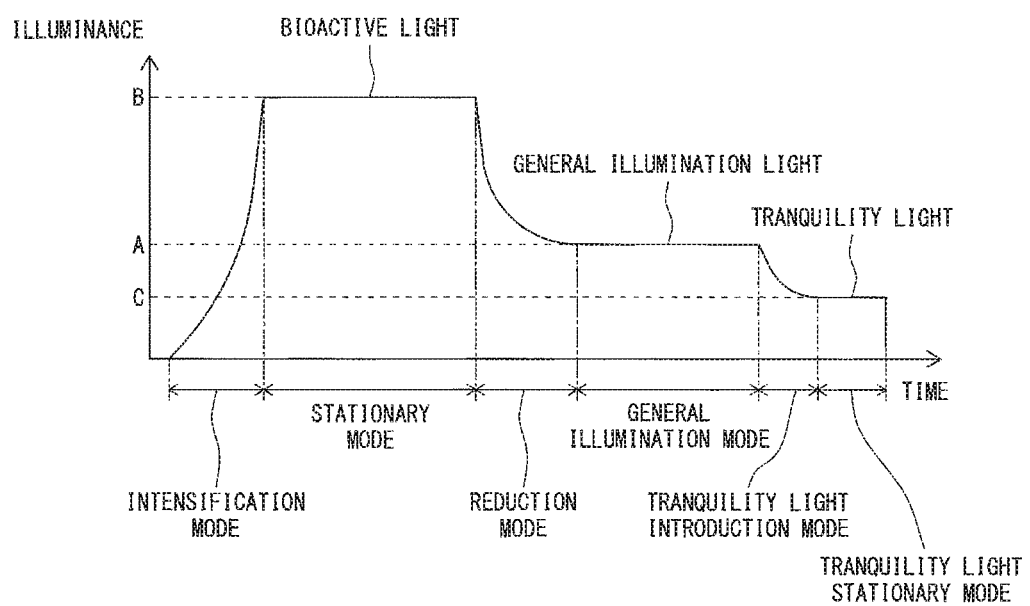
FIG. 4 is a diagram illustrating an example of an illuminance change in a light source of the illumination system over time.

The configuration and the functions of the controller 14 will now be described in more details with reference to FIGS. 3 and 4. FIG. 3 is a block diagram illustrating a configuration of the controller 14. FIG. 4 is a diagram illustrating an illuminance change in the light source 13 over time when it is executed by the function of the controller 14. In FIG. 4, it is assumed that phototherapy is applied by using the bioactive light.

As illustrated in FIGS. 3 and 4, the controller 14 executes the intensification mode in which the illuminance B of the bioactive light is set by gradually increasing the illuminance of the light source 13 over time by virtue of the function of intensification mode execution unit 41. It is necessary to set an increase rate of the illuminance of the light source 13 in the intensification mode; that is, the gradual increase rate such that a phototherapy target person 3 does not feel uncomfortable. Note that the increase rate may change depending on the phototherapy target person 3 or the like. The intensification mode execution unit 41 may approximately linearly increase the illuminance of the light source 13 over time. Preferably, the intensification mode execution unit 41 increases the illuminance of the light source 13 in a gentle curve shape.

The controller 14 changes the illuminance, for example, based on a light control rate of the light source 13. Typically, since a relationship between the light control rate and the illuminance of the light source 13 is known in advance, the illuminance can be adjusted by changing the light control rate of the light source 13 over time based on an estimated face illuminance value. The intensification mode execution unit 41 may execute the intensification mode by gradually increasing the light control rate of the light source 13 depending on a light control curve by which the light control rate gradually increases over time. The light control curve may be stored in the memory unit 35 in advance. In this case, the time necessary for the intensification mode is similar to that of the existing one. Therefore, it is possible to determine whether or not the illuminance of the light source 13 reaches the illuminance B of the bioactive light, by determining the time elapsing from the start of the intensification mode.

For example, the intensification mode execution unit 41 acquires the elapsed time of the intensification mode from the time measurement unit 34 and terminates the intensification mode when the elapsed time reaches the time necessary for the intensification mode. The time measurement unit 34 measures time elapsing from the start of the intensification mode to the end of the intensification mode. In addition, the time measurement unit 34 measures various periods of time used in the control of the controller 14 for the modes such as the stationary mode and the reduction mode. Alternatively, whether or not the illuminance of the light source 13 reaches the illuminance B of the bioactive light may also be determined by actually measuring the illuminance in the room 1 using an illuminance sensor. The face illuminance of the phototherapy target person 3 may be actually measured using an illuminance sensor.

The increase rate of the illuminance (light control curve) in the intensification mode is set, for example, to be gentler in the start and end periods of the intensification mode relative to the middle period (refer to FIGS. 6A and 6B described below). Alternatively, the increase speed of the illuminance gradually increases from the start of the intensification mode. That is, the light control curve may be set to have a gradually increasing slope. The increase rate of the illuminance is set to, for example, 10 (1x/min) to 200 (1x/min), and preferably 30 (1x/min) to 100 (1x/min), and may be changed depending on the elapsed time of the intensification mode within this range.

In the example of FIG. 4, the intensification mode is executed while the light source 13 is turned off. However, the intensification mode execution unit 41 may execute the intensification mode from the lighting state of the general illumination light. That is, in a case where the light source 13 is turned off, the intensification mode may be executed such that the illuminance of the light source 13 directly increases to the illuminance A of the general illumination light, and then gradually increases the illuminance over time.

It is known that light of a high color temperature containing a lot of blue light has a high degree of melatonin action, and the bioactive light preferably contains blue light. Therefore, in the intensification mode, the illuminance may increase while increasing the color temperature of the light source 13. In a case where the light source 13 includes at least a first light source for emitting blue light and a second light source for emitting light having a ratio of the blue light smaller than that of the first light source, the intensification mode execution unit 41 may set a change amount of the illuminance of the first light source to be larger than a change amount of the illuminance of the second light source.

The controller 14 executes the stationary mode for constantly maintaining the illuminance of the light source 13 at the illuminance B of the bioactive light by virtue of the function of stationary mode execution unit 42. The stationary mode execution unit 42 executes the stationary mode if the illuminance of the light source 13 reaches the illuminance B of the bioactive light. That is, when the illuminance of the light source 13 reaches the illuminance B, the control mode is switched to the stationary mode from the intensification mode. The time measurement unit 34 may reset a timer to measure the time from the start to the end of the stationary mode when the mode is switched to the stationary mode.

The stationary mode execution unit 42 continuously maintains the stationary mode until a predetermined period of time elapses. The predetermined period of time is not particularly limited as long as the phototherapy effect can be sufficiently obtained. In general, the predetermined period of time is set to be shorter as the illuminance B of the bioactive light increases. In addition, the predetermined period of time is set to be longer as the illuminance B decreases. For example, the predetermined period of time is set to about 15 minutes to 7 hours, assuming that the illuminance B is set to 1,000 (1x) to 10,000 (1x). For example, the stationary mode execution unit 42 obtains the elapsed time of the stationary mode from the time measurement unit 34 and terminates the stationary mode when the elapsed time reaches the time necessary for the stationary mode.

The controller 14 executes the reduction mode for gradually decreasing the illuminance of the light source 13 from the illuminance B of the bioactive light to the illuminance A of the general illumination light over time by virtue of the function of reduction mode execution unit 43. Since a difference of the illuminance is significant between the bioactive light and the general illumination light, it is possible to enable smooth adaptation of a phototherapy target person 3 without generating discomfort by gradually decreasing the illuminance of the light source 13 even when the illuminance is returned to the general illumination light. That is, the controller 14 executes a series of illuminance change processes including the intensification mode, the stationary mode, and the reduction mode when the phototherapy is executed.

The reduction mode execution unit 43 executes the reduction mode if the elapsed time acquired from the time measurement unit 34 reaches the time necessary for the stationary mode. That is, the control mode is switched from the stationary mode to the reduction mode when a predetermined period of time elapses from the start of the stationary mode. The time measurement unit 34 may reset the time to measure the time from the start to the end of the reduction mode when the control mode is switched to the reduction mode.

A decrease rate; that is, a decrease speed of the illuminance of the reduction mode, is necessary to be set such that a phototherapy target person 3 does not feel uncomfortable. Note that the decrease rate may be changed depending on a phototherapy target person 3 or the like. The reduction mode execution unit 43 may approximately linearly decrease the illuminance of the light source 13 over time. Preferably, the reduction mode execution unit 43 decreases the illuminance of the light source 13 in a gentle curve shape. The reduction mode execution unit 43 may execute the reduction mode by gradually decreasing the light control rate of the light source 13 to follow the light control curve by which the light control rate gradually decreases over time.

For example, the reduction mode execution unit 43 acquires the elapsed time of the reduction mode from the time measurement unit 34 and terminates the reduction mode when the elapsed time reaches the time necessary for the reduction mode. The decrease rate (light control curve) of the illuminance of the reduction mode is set to be gentler at the start and end periods of the reduction mode relative to the middle period. The decrease rate of the illuminance is set to, for example, 1 (1x/min) to 200 (1x/min), and preferably, 5 (1x/min) to 100 (1x/min). The decrease rate of the illuminance may be changed depending on the elapsed time of the reduction mode within this range.

The controller 14 executes the general illumination mode for emitting the general illumination light by virtue of the function of the general illumination mode execution unit 40. The general illumination mode may continue, for example, until the light-on button 30 is manipulated to turn off the illumination. Alternatively, the execution time may be set in advance using a timer. In this case, the control mode may automatically advance to the tranquility light introduction mode after a predetermined period of time by measuring time using the time measurement unit 34.

The controller 14 executes the tranquility light introduction mode in which the illuminance C of the tranquility light is set by further gradually reducing the illuminance of the light source 13 from the illuminance level of the general illumination light over time. Then, the tranquility light stationary mode is executed in which the illuminance C is maintained for a predetermined period of time. The tranquility light introduction mode is executed by virtue of the function of tranquility light introduction mode execution unit 44, and the tranquility light stationary mode is executed by virtue of the function of tranquility light stationary mode execution unit 45. The tranquility light illumination environment is suitable before going to bed. Since the illuminance of the tranquility light is much lower than the illuminance of the general illumination light, it is possible to enable smooth adaptation of a phototherapy target person 3 without generating discomfort by gradually reducing the illuminance of the light source 13.

Since it is desirable that the tranquility light contains no blue light that suppresses melatonin secretion, or has a low color temperature with little blue light component, the illuminance of the tranquility light introduction mode may be reduced while the color temperature of the light source 13 is reduced. In a case where the light source 13 includes at least a first light source for emitting blue light and a second light source for emitting light having a ratio of the blue light smaller than that of the first light source, the tranquility light introduction mode execution unit 44 may set a change amount of the illuminance of the first light source to be larger than a change amount of the illuminance of the second light source.

The tranquility light introduction mode execution unit 44 may automatically execute the tranquility light introduction mode, for example, by virtue of the timer function using the time measurement unit 34. In addition, a manipulation unit for turning on the tranquility light may be provided in the manipulation apparatus 12, and the tranquility light introduction mode may be executed in response to a manipulation on the manipulation unit. Similar to the reduction mode, it is necessary to set the decrease rate of the illuminance in the tranquility light introduction mode such that a phototherapy target person 3 does not feel uncomfortable. For example, the tranquility light introduction mode execution unit 44 gradually reduces the light control rate of the light source 13 based on a light control curve by which the light control rate gradually decreases over time.

The tranquility light stationary mode execution unit 45 continuously executes the tranquility light stationary mode until a predetermined period of time elapses. The predetermined period of time is not particularly limited as long as the effect of the tranquility light is sufficiently obtained. For example, the predetermined period of time is set to 30 minutes to 2 hours. For example, the tranquility light stationary mode execution unit 45 may acquire the elapsed time of the tranquility light stationary mode from the time measurement unit 34 and may turn off the light source 13 by terminating the tranquility light stationary mode when the acquired time reaches the predetermined period of time.

Figure 5:
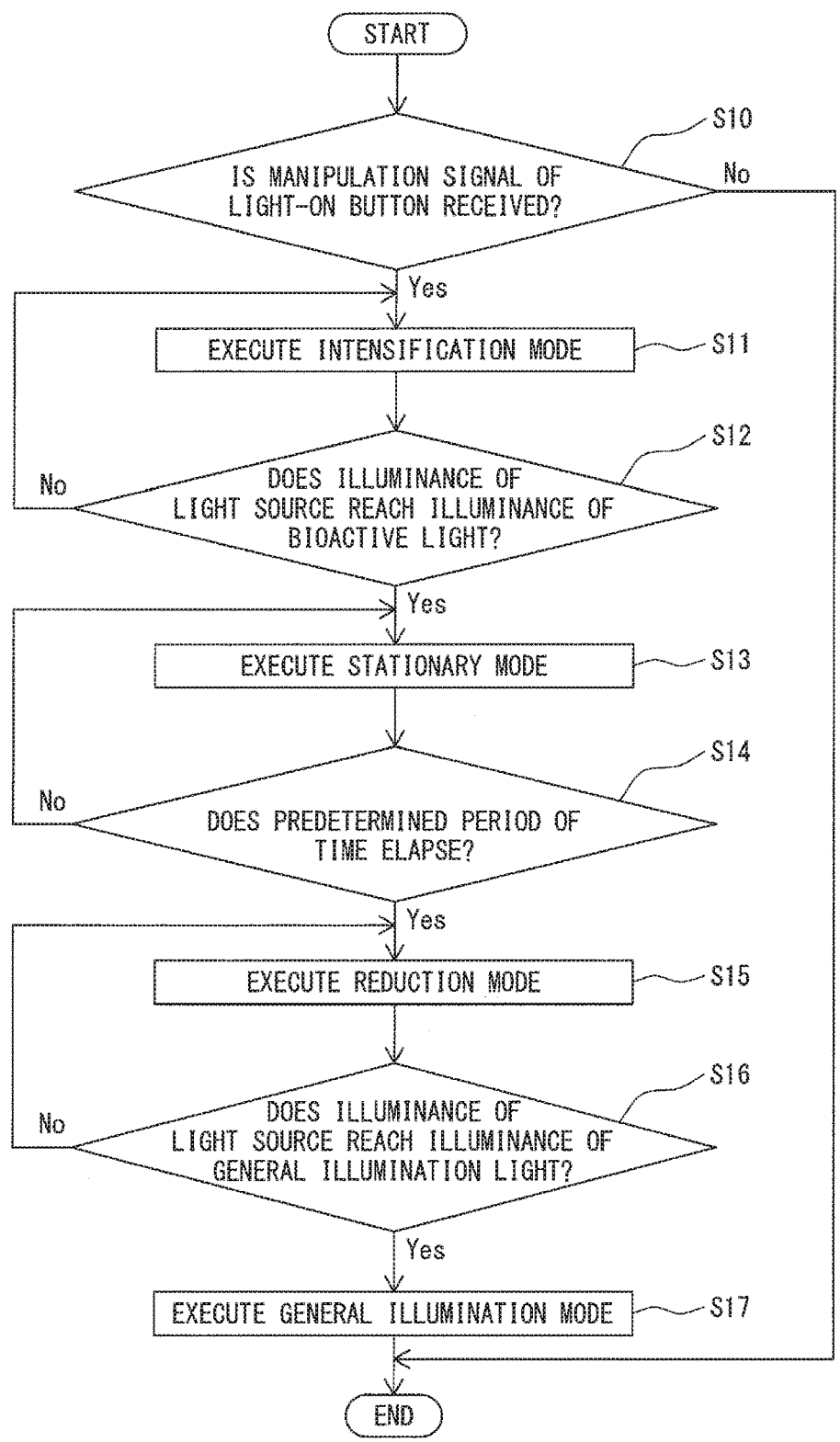
FIG. 5 is a diagram illustrating an example of control flow of the illumination system.

FIG. 5 is a diagram illustrating an exemplary control flow of the illumination system 10 having the aforementioned configuration. FIG. 5 illustrates a control flow in which the control state advances to the bioactive light illumination environment from a turn-off state of the light source 13 in order to perform phototherapy, and is then returned to the general illumination environment.

As illustrated in FIG. 5, if the manipulation signal of the light-on button 30 is received, the light source 13 is turned on, and the intensification mode is executed in which the illuminance B of the bioactive light is set by gradually increasing the illuminance of the light source 13 over time (S10, S11). In S11, the illuminance of the light source 13 may directly increase to the illuminance A of the general illumination light, and then gradually increase from the illuminance A to the illuminance B over time. The steps S10 and S 11 are executed by virtue of the function of the intensification mode execution unit 41. Alternatively, the intensification mode may automatically start by virtue of the timer function.

Then, if the illuminance of the light source 13 reaches the illuminance B of the bioactive light, the stationary mode is executed in which the illuminance of the light source 13 is constantly maintained at the illuminance B (S12, S13). That is, the control mode is switched from the intensification mode to the stationary mode when the illuminance of the light source 13 reaches the illuminance B. The control mode may be switched by actually measuring the illuminance of the light source using the illuminance sensor. Preferably, as described above, the control mode is switched based on the measured time of the time measurement unit 34. The steps S12 and S13 are executed by virtue of the function of the stationary mode execution unit 42.

Then, if a predetermined period of time elapses after the start of the stationary mode of S13, the reduction mode is executed in which the illuminance C of the general illumination light is set by gradually reducing the illuminance of the light source 13 over time (S14, S15). That is, when the irradiation time of the bioactive light reaches a predetermined period of time, the control mode is switched to the reduction mode from the stationary mode. The steps S14 and S15 are executed by virtue of the function of the reduction mode execution unit 43. In addition, if the illuminance of the light source 13 reaches the illuminance A of the general illumination light, the general illumination mode is executed in which the illuminance of the light source 13 is constantly maintained at the illuminance A (S16, S17). The steps S16 and S17 are executed by virtue of the function of the general illumination mode execution unit 40.

Using the illumination system 10, it is possible to make a phototherapy target person 3 smoothly familiar with the bioactive light illumination environment without feeling uncomfortable by employing the intensification mode and the reduction mode. However, there are some individual differences in impression of the lighting. In addition, as age increases, the incidence of cataract increases. When a person suffers from cataract, the person becomes more sensitive to glare. For this reason, generally, older people tend to feel that the bioactive light is too bright. Under such circumstances, the manipulation apparatus 12 preferably has the illuminance adjustment unit 31, the age input unit 32, and the color temperature adjustment unit 33.

Configurations of the illuminance adjustment unit 31 or the like and control states generated by manipulating them will now be described in details with reference to FIGS. 6A to 10B.

Figure 6A:
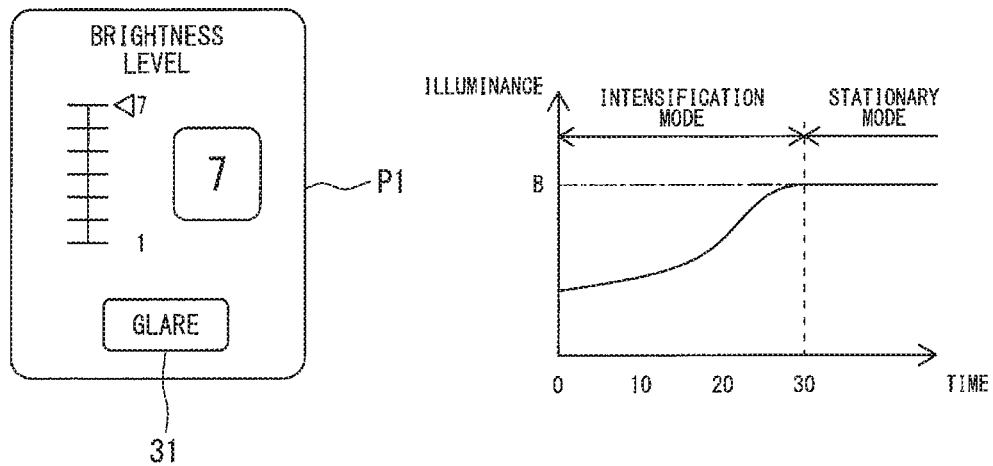
FIG. 6A is a diagram illustrating an example of a manipulation screen and control based on a manipulation on the screen.
Figure 6B:
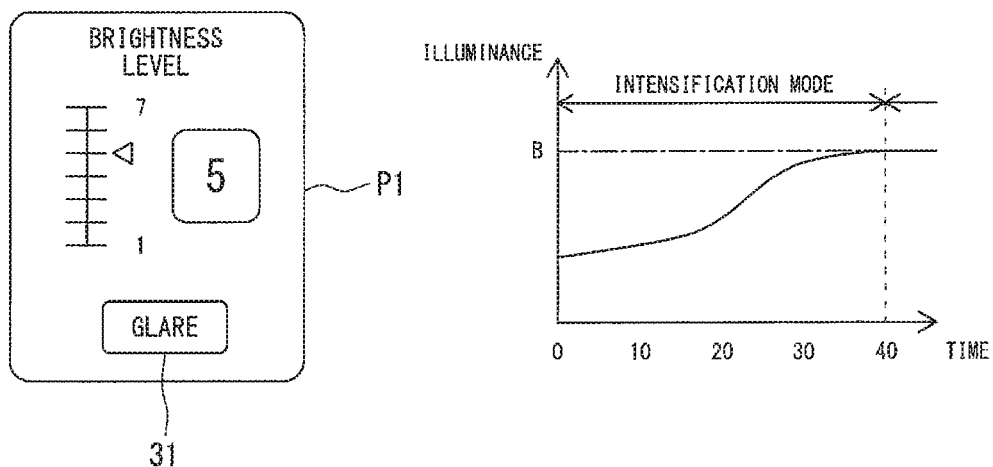
FIG. 6B is a diagram illustrating an example of a manipulation screen and control based on a manipulation on the screen.

FIGS. 6A and 6B are diagrams illustrating a manipulation screen P1 having the illuminance adjustment unit 31 and an exemplary control based on a manipulation on the manipulation screen P1. FIG. 6A illustrates a state before the manipulation screen P1 is manipulated, and FIG. 6B illustrates a state after the manipulation screen P1 is manipulated (this similarly applies to FIGS. 7A to 10B). As illustrated in FIG. 6A, a current illuminance level of the light source 13 and the illuminance adjustment unit 31 for reducing the illuminance of the light source 13 are displayed on the manipulation screen P1. On the manipulation screen P1, for easy manipulation of a user, the illuminance level is displayed as characters "BRIGHTNESS LEVEL," and the manipulation button of the illuminance adjustment unit 31 is displayed as characters "GLARE."

As illustrated in FIG. 6B, the brightness level can be lowered by pressing the manipulation button "GLARE" (hereinafter, sometimes referred to as a "glare button"). That is, it is possible to reduce the illuminance of the light source 13. Reduction of the illuminance of the light source 13 based on the input information of the illuminance adjustment unit 31 is executed by virtue of the function of first adjustment unit 46 of the controller 14. The first adjustment unit 46 reduces the illuminance of the light source 13, for example, based on the input information of the manipulation screen P1 within a range of the illuminance of the bioactive light. That is, in a case where the range effective as the bioactive light is equal to or higher than the illuminance Bz (refer to FIGS. 7A and 7B), the illuminance of the light source 13 is reduced within a range equal to or higher than the illuminance Bz.

The first adjustment unit 46 may execute the intensification mode by reducing the increase rate of the illuminance based on the input information of the illuminance adjustment unit 31. In the example of FIG. 6B, the intensification mode is executed by reducing the increase rate of the illuminance when the glare button is manipulated, compared to a case where the glare button is not manipulated. In this case, the resulting illuminance may be set to be equal by lengthening the time for the intensification mode. Similarly, when the glare button is manipulated during execution of the stationary mode, the intensification mode may be executed by reducing the increase rate of the illuminance, so that the illuminance level is returned to the illuminance prior to the manipulation over time.

Figure 7A:
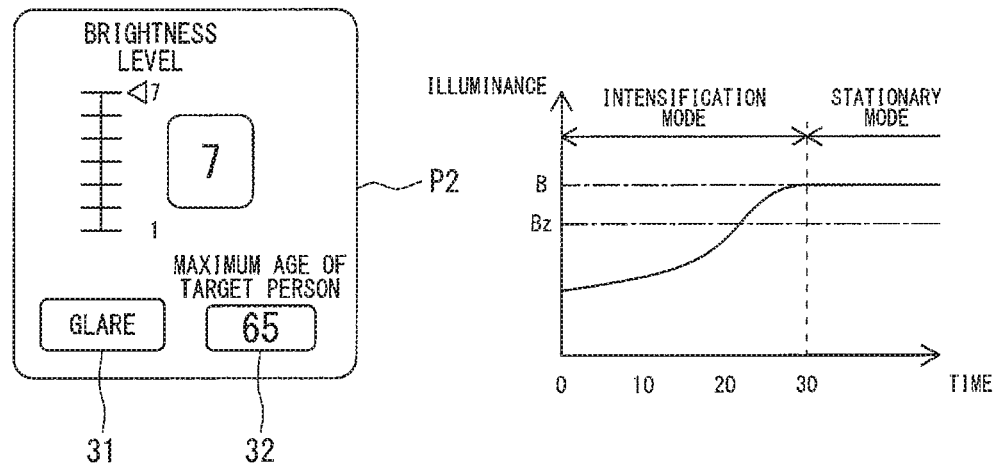
FIG. 7A is a diagram illustrating an example of a manipulation screen and control based on a manipulation on the screen.
Figure 7B:
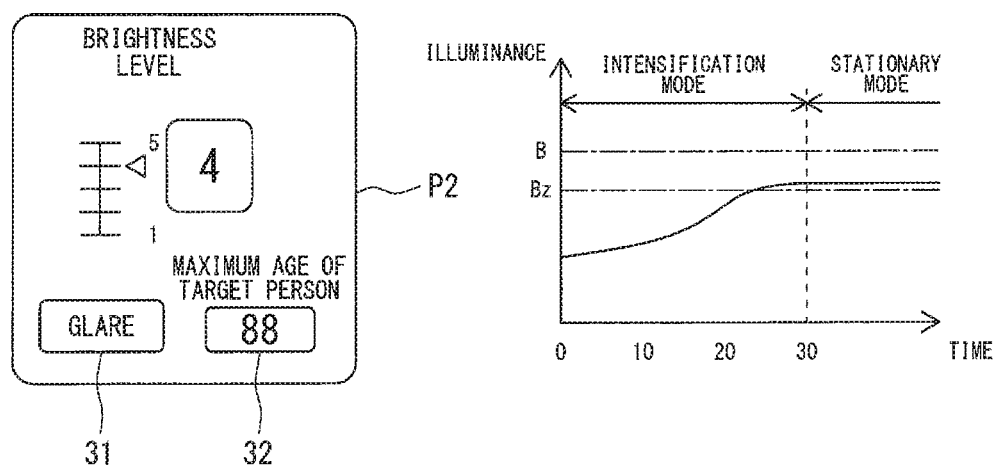
FIG. 7B is a diagram illustrating an example of a manipulation screen and control based on a manipulation on the screen.

FIGS. 7A and 7B are diagrams illustrating a manipulation screen P2 having the age input unit 32 and an exemplary control based on a manipulation on the manipulation screen P2. As illustrated in FIG. 7A, the age input unit 32 for inputting an age of a phototherapy target person 3 who is target person to be irradiated with bioactive light is displayed on the manipulation screen P2. The age input unit 32 may be configured such that a ten-key pad or the like for inputting the age is displayed when it is touched. On the manipulation screen P2, a maximum age of the phototherapy target person 3 is input using the age input unit 32. In addition, on the manipulation screen P2, the current illuminance level of the light source 13 and the illuminance adjustment unit 31 for reducing the illuminance of the light source 13 are displayed along with the age input unit 32.

As illustrated in FIG. 7B, as the maximum age of the phototherapy target person 3 is input to the age input unit 32, the illuminance of the light source 13 is reduced based on this input information. Reduction of the illuminance of the light source 13 based on the input information of the age input unit 32 is executed by virtue of the function of second adjustment unit 47 of the controller 14. The second adjustment unit 47 reduces the illuminance of the light source 13 based on the input information of the manipulation screen P2 within a range of the illuminance of the bioactive light, for example, within a range equal to or higher than the illuminance Bz. In the example of FIG. 7B, as the maximum age of the phototherapy target person 3 is changed from "65" years old of FIG. 7A to "88" years old, the upper limitation of the brightness level is lowered from "7" to "5."

Figure 8A:
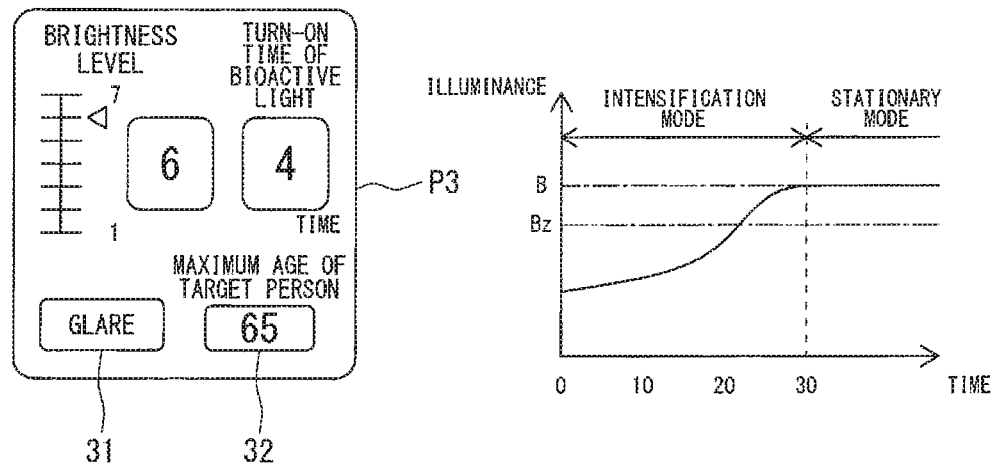
FIG. 8A is a diagram illustrating an example of a manipulation screen and control based on a manipulation on the screen.
Figure 8B:
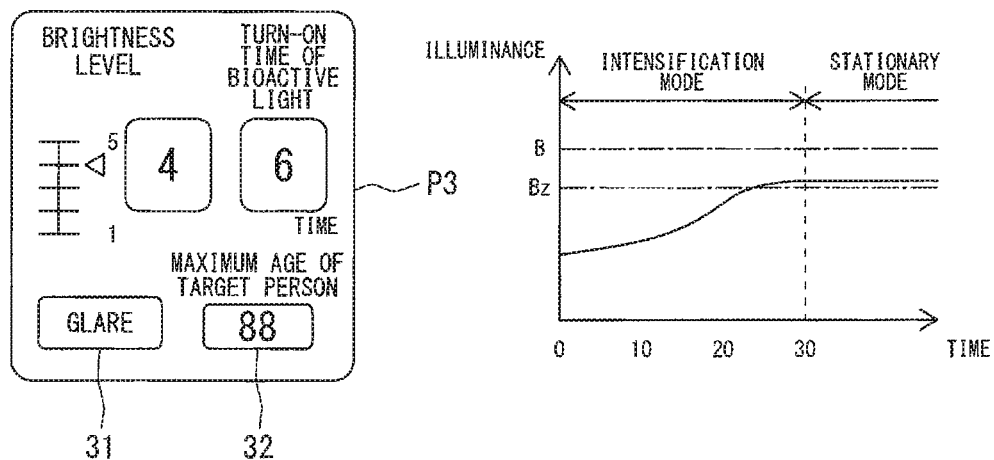
FIG. 8B is a diagram illustrating an example of a manipulation screen and control based on a manipulation on the screen.

FIGS. 8A and 8B are diagrams illustrating a manipulation screen P3 having the illuminance adjustment unit 31 and the age input unit 32 and an exemplary control based on a manipulation on the manipulation screen P3. The manipulation screen P3 of FIG. 8A is similar to the manipulation screen P2 of FIG. 7A in that the illuminance adjustment unit 31 and the age input unit 32 are provided. In comparison, the manipulation screen P3 is different from the manipulation screen P2 in that the turn-on time of the bioactive light is displayed.

In a case where the illuminance of the light source 13 is reduced within a range of the illuminance of the bioactive light based on the input information of the manipulation apparatus 12, the controller 14 may extend the bioactive light irradiation time depending on the reduction level. The brightness level on the manipulation screen P3 of FIG. 8A is set to "6," and the brightness level on the manipulation screen P3 of FIG. 8B is set to "4." In addition, the bioactive light irradiation time displayed as the turn-on time; that is, the stationary mode period is extended from 4 hours to 6 hours.

According to an embodiment of the disclosure, the first adjustment unit 46 may extend the bioactive light irradiation time in a case where the illuminance of the light source 13 is reduced based on the input information of the illuminance adjustment unit 31. In addition, the second adjustment unit 47 may extend the bioactive light irradiation time in a case where the illuminance of the light source 13 is reduced based on the input information of the age input unit 32. By extending the bioactive light irradiation time, it is possible to sufficiently obtain the phototherapy effect even when the illuminance of the light source 13 is reduced.

Figure 9A:
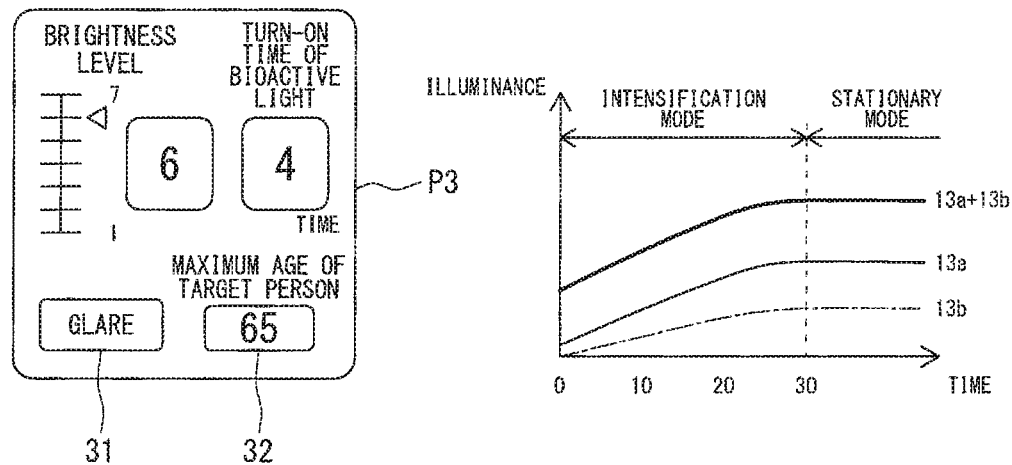
FIG. 9A is a diagram illustrating an example of a manipulation screen and control based on a manipulation on the screen.
Figure 9B:
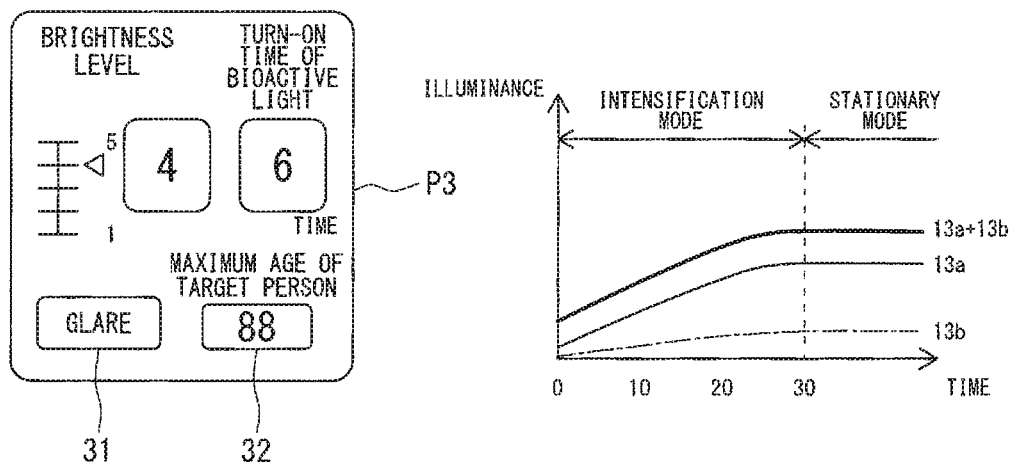
FIG. 9B is a diagram illustrating an example of a manipulation screen and control based on a manipulation on the screen.

FIGS. 9A and 9B illustrate the manipulation screen P3 similar to that of FIGS. 8A and 8B as a manipulation screen. In FIGS. 9A and 9B, it is assumed that the light source 13 includes at least a first light source for emitting blue light (hereinafter, referred to as a "first light source 13a") and a second light source for emitting light having a ratio of blue light smaller than that of the first light source 13a (hereinafter, referred to as a "second light source 13b"). In the example of FIGS. 9A and 9B, the intensification mode and the stationary mode are executed such that a total illuminance of the first and second light sources 13a and 13b is within a range of the illuminance of the bioactive light. The brightness level on the manipulation screen P3 of FIG. 9A is set to "6," and the brightness level on the manipulation screen P3 of FIG. 9B is set to "4."

The controller 14 may reduce the total illuminance of the first and second light sources 13a and 13b while controlling a change rate of the illuminance of the first light source 13a to be smaller than that of the second light source 13b based on the input information of the manipulation apparatus 12 such as the illuminance adjustment unit 31 or the age input unit 32. This control is executed by virtue of the function of the first adjustment unit 46 in a case where the illuminance adjustment unit 31 is manipulated. This control is executed by virtue of the function of the second adjustment unit 47 in a case where the age input unit 32 is manipulated.

That is, the illuminance of the first light source 13a is changed more than the illuminance of the second light source 13b in a case where the illuminance of the light source 13 is reduced within a range of the illuminance of the bioactive light based on the input information of the manipulation apparatus 12. In addition, only the illuminance of the first light source 13a may be reduced while maintaining the illuminance of the first light source 13a. Since light having a high color temperature is known to have a high degree of melatonin action similar to the blue light, it is possible to attenuate glare by reducing the total illuminance while securing the phototherapy effect by maintaining the illuminance of the first light source 13a emitting light having a large amount of blue light as long as possible.

Figure 10A:
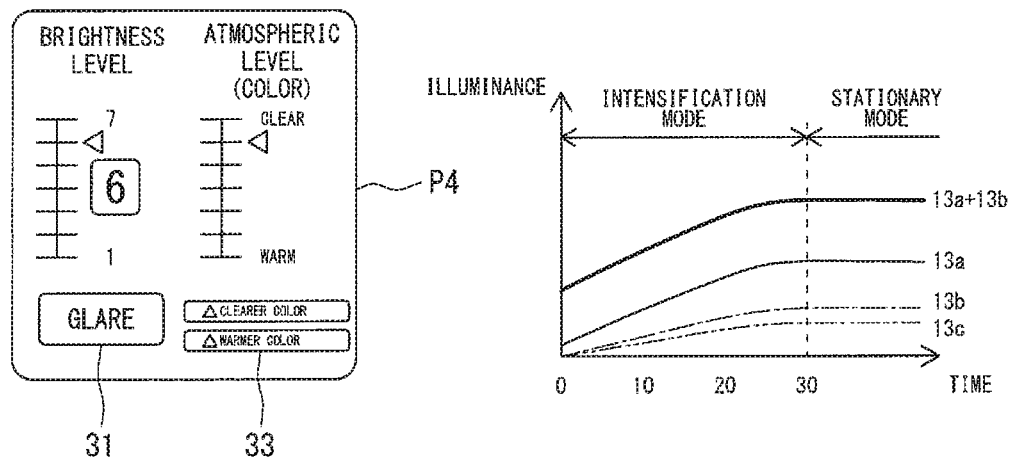
FIG. 10A is a diagram illustrating an example of a manipulation screen and control based on a manipulation on the screen.
Figure 10B:
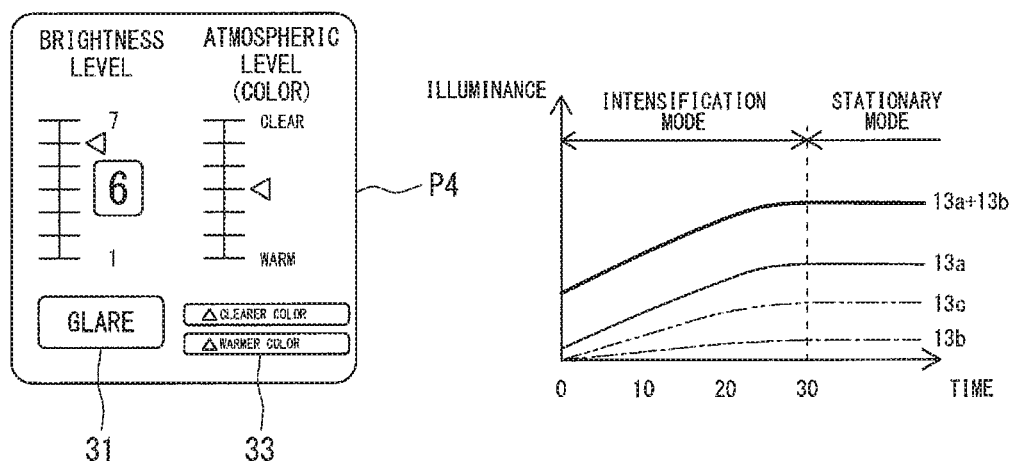
FIG. 10B is a diagram illustrating an example of a manipulation screen and control based on a manipulation on the screen.

FIGS. 10A and 10B are diagrams illustrating a manipulation screen P4 having a color temperature adjustment unit 33 and an exemplary control based on a manipulation of the manipulation screen P4. In FIGS. 10A and 10B, it is assumed that the light source 13 includes the first light source 13a, the second light source 13b, and a third light source for emitting light having a ratio of blue light smaller than that of the first light source 13a and having a color temperature lower than that of the second light source 13b (hereinafter, referred to as a "third light source 13c"). As illustrated in FIG. 10A, the color temperature adjustment unit 33 for lowering the color temperature of the light source 13 is displayed on the manipulation screen P4.

On the manipulation screen P4, the color temperature is displayed as "ATMOSPHERIC LEVEL." In addition, characters "CLEARER COLOR" or "WARMER COLOR" are displayed on the manipulation button of the color temperature adjustment unit 33. In this case, when the button "CLEARER COLOR" is pressed, the color temperature increases. When the button "WARMER COLOR" is pressed, the color temperature decreases. The current illuminance level of the light source 13 and the illuminance adjustment unit 31 for reducing the illuminance of the light source 13 are also displayed on the manipulation screen P4 along with the age input unit 32. The age input unit 32 and the bioactive light turn-on time may also be displayed on the manipulation screen P4.

AS illustrated in FIG. 10B, the controller 14 may decrease the illuminance of the second light source 13b and increase the illuminance of the third light source 13c based on the input information of the color temperature adjustment unit 33 by virtue of the function of the third adjustment unit 48. In this case, the illuminance of the first light source 13a can be maintained. Alternatively, the illuminance of the third light source 13c may increase instead of decreasing the illuminance of the second light source 13b. As a result, it is possible to secure the phototherapy effect by maintaining the total illuminance of the light sources 13a, 13b, and 13c while implementing a warm atmosphere by lowering the color temperature. In a case where the light source 13 includes a high color temperature light source and a low color temperature light source that emits light having a color temperature lower than that of the high color temperature light source, the third adjustment unit 48 increases the illuminance of the low color temperature light source by reducing the illuminance of the high color temperature light source based on the input information of the color temperature adjustment unit 33.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. An illumination system comprising:
   a light source configured to emit general illumination light and bioactive light having an illuminance higher than an illuminance of the general illumination light;
   a controller configured to control a lighting state of the light source; and
   a manipulation apparatus including an illuminance adjustment unit for decreasing the illuminance of the light source,
   wherein the controller is further configured to execute an intensification mode in which the illuminance of the bioactive light is set by increasing the illuminance of the light source,
   wherein the controller is further configured to execute a stationary mode in which the illuminance of the light source is maintained at the illuminance of the bioactive light, and
   wherein the controller is further configured to reduce an increase rate of the illuminance of the light source in the intensification mode based on input information of the illuminance adjustment unit.

2. The illumination system according to claim 1, wherein the controller is further configured to execute a reduction mode in which the illuminance of the light source decreases from the illuminance of the bioactive light to the illuminance of the general illumination light.

3. The illumination system according to claim 1, wherein the manipulation apparatus includes an illuminance adjustment unit for decreasing the illuminance of the light source, and
   the controller is further configured to reduce the illuminance of the light source based on input information of the illuminance adjustment unit within a range of the illuminance of the bioactive light.

4. The illumination system according to claim 1, wherein the manipulation apparatus includes an age input unit for inputting an age of a target person to be irradiated with the bioactive light, and
   the controller is further configured to reduce the illuminance of the light source based on input information of the age input unit within a range of the illuminance of the bioactive light.

5. The illumination system according to claim 1, wherein the light source includes at least a first light source for emitting blue light and a second light source for emitting light having a ratio of blue light smaller than that of the first light source, and
   the controller is further configured to decrease a total illuminance of the first and second light sources while controlling a change rate of an illuminance of the first light source to be lower than a change rate of an illuminance of the second light source based on the input information of the manipulation apparatus.

6. The illumination system according to claim 1, wherein the light source includes a high color temperature light source and a low color temperature light source for emitting light having a color temperature lower than a color temperature of the high color temperature light source,
   the manipulation apparatus includes a color temperature adjustment unit for reducing a color temperature of the light source, and
   the controller is further configured to decrease an illuminance of the high color temperature light source and to increase an illuminance of the low color temperature light source, based on input information of the color temperature adjustment unit.

7. An illumination system comprising:
   a light source configured to emit general illumination light and bioactive light having an illuminance higher than an illuminance of the general illumination light;
   a controller configured to control a lighting state of the light source; and
   a manipulation apparatus including an illuminance adjustment unit for decreasing an illuminance of the light source,
   wherein the controller is further configured to execute an intensification mode in which the illuminance of the bioactive light is set by increasing the illuminance of the light source,
   wherein the controller is further configured to execute a stationary mode in which the illuminance of the light source is maintained at the illuminance of the bioactive light, and
   wherein the controller is further configured to extend an irradiation time of the bioactive light depending on a decrease rate of the illuminance of the light source when the illuminance of the light source is decreased within a range of the illuminance of the bioactive light based on input information of the manipulation apparatus.

8. The illumination system according to claim 7, wherein the controller is further configured to execute a reduction mode in which the illuminance of the light source decreases from the illuminance of the bioactive light to the illuminance of the general illumination light.

9. The illumination system according to claim 7, wherein the manipulation apparatus includes an illuminance adjustment unit for decreasing the illuminance of the light source, and
   the controller is further configured to reduce the illuminance of the light source based on input information of the illuminance adjustment unit within a range of the illuminance of the bioactive light.

10. The illumination system according to claim 7, wherein the manipulation apparatus includes an age input unit for inputting an age of a target person to be irradiated with the bioactive light, and
    the controller is further configured to reduce the illuminance of the light source based on input information of the age input unit within a range of the illuminance of the bioactive light.

11. The illumination system according to claim 7, wherein the light source includes at least a first light source for emitting blue light and a second light source for emitting light having a ratio of blue light smaller than that of the first light source, and
   the controller is further configured to decrease a total illuminance of the first and second light sources while controlling a change rate of an illuminance of the first light source to be lower than a change rate of an illuminance of the second light source based on the input information of the manipulation apparatus.

12. The illumination system according to claim 7, wherein the light source includes a high color temperature light source and a low color temperature light source for emitting light having a color temperature lower than a color temperature of the high color temperature light source,
   the manipulation apparatus includes a color temperature adjustment unit for reducing a color temperature of the light source, and
   the controller is further configured to decrease an illuminance of the high color temperature light source and to increase an illuminance of the low color temperature light source, based on input information of the color temperature adjustment unit.

* * * * *